US012622810B2

(12) United States Patent
    Alhourani

(10) Patent No.:    US 12,622,810 B2
(45) Date of Patent:    May 12, 2026

(54) RAKAN GLAUCOMA DEVICE

(71) Applicant: Rakan Alhourani, Apple Valley, CA (US)

(72) Inventor: Rakan Alhourani, Apple Valley, CA (US)

( * ) Notice: Subject to any disclaimer, the term of this patent is extended or adjusted under 35 U.S.C. 154(b) by 365 days.

(21) Appl. No.: 18/507,069

(22) Filed: Nov. 12, 2023

(65) Prior Publication Data

US 2024/0139030 A1    May 2, 2024

(51) Int. Cl.
    *A61F 9/007*    (2006.01)
(52) U.S. Cl.
    CPC .. *A61F 9/00781* (2013.01); *A61F 2250/0013* (2013.01); *A61F 2250/0097* (2013.01)

(58) Field of Classification Search
    CPC .......... A61F 9/00781; A61F 2250/0013; A61F 2250/0097; A61B 3/16
    See application file for complete search history.

(56) References Cited

U.S. PATENT DOCUMENTS

2018/0271700 A1*  9/2018  Alhourani ................ A61B 3/16
2020/0229982 A1*  7/2020  Mixter ............... A61F 9/00781

* cited by examiner

*Primary Examiner* — Rebecca E Eisenberg
*Assistant Examiner* — Katherine-Ph Minh Pham

(57)    ABSTRACT

The present invention is a device that is used for glaucoma management by using an adjustable drainage device. And this device has an indicator to help patient checking the intraocular pressure hence seeking medical advice immediately as needed.

1 Claim, 27 Drawing Sheets

RAKAN GLAUCOMA DEVICE

CROSS-REFERENCES TO RELATED APPLICATIONS

Not Applicable

STATEMENT REGARDING FEDERALLY SPONSORED RESEARCH OR DEVELOPMENT

Not Applicable

NAME OF THE INVENTOR

Rakan Alhourani

STATEMENT REGARDING PRIOR DISCLOSURES BY THE INVENTOR OR A JOINT INVENTOR

Not Applicable

FIELD OF THE INVENTION

The present invention generally relates to a device that drains aqueous humor from inside the eye in order to adjust intraocular pressure (IOP). In this device, the drainage flow rate and amount are adjustable and the IOP can be checked by the patient at any time.

BACKGROUND OF THE INVENTION

Rakan glaucoma device has an application in managing glaucoma and checking the IOP directly by patient. This device can drain excessive intraocular fluid hence regulating and adjusting the IOP, as the drainage flow rate is self-adjusted depending on IOP and can be readjusted anytime. Also the existence of valve prevents back flow of aqueous humor and it prevents unwanted decrease in IOP (hypotony).

SUMMARY OF THE INVENTION

The present invention is a drainage device that manages glaucoma using adjustable valves and shunts that precisely control aqueous humor outflow hence IOP. Also, this new device allows patients to self-check IOP.

DETAILED DESCRIPTION OF THE INVENTION

Figure 1:
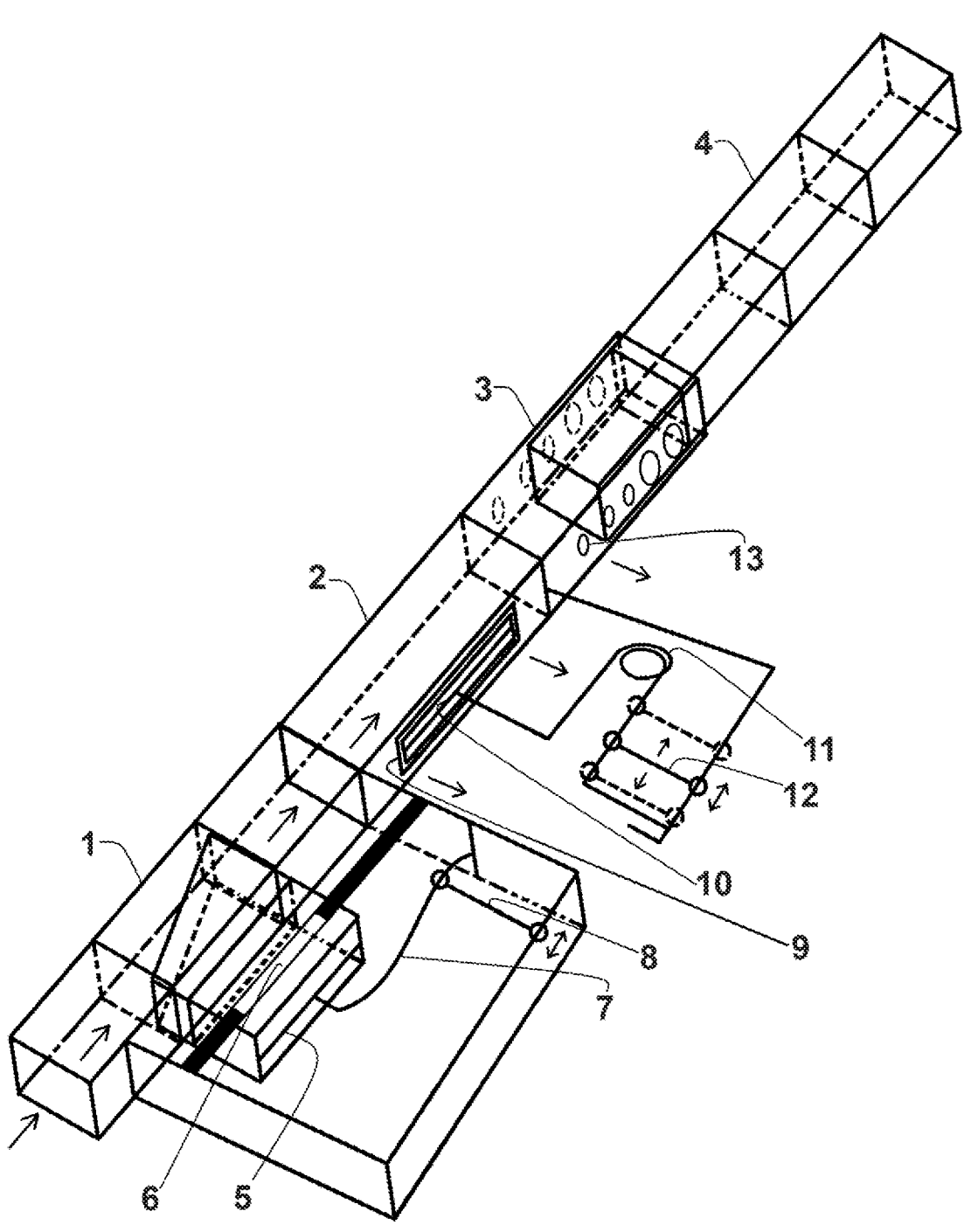
FIG. 1: General view of Rakan glaucoma device with sliding-seal piece blunt-sealing big portion of third part.
Figure 2:
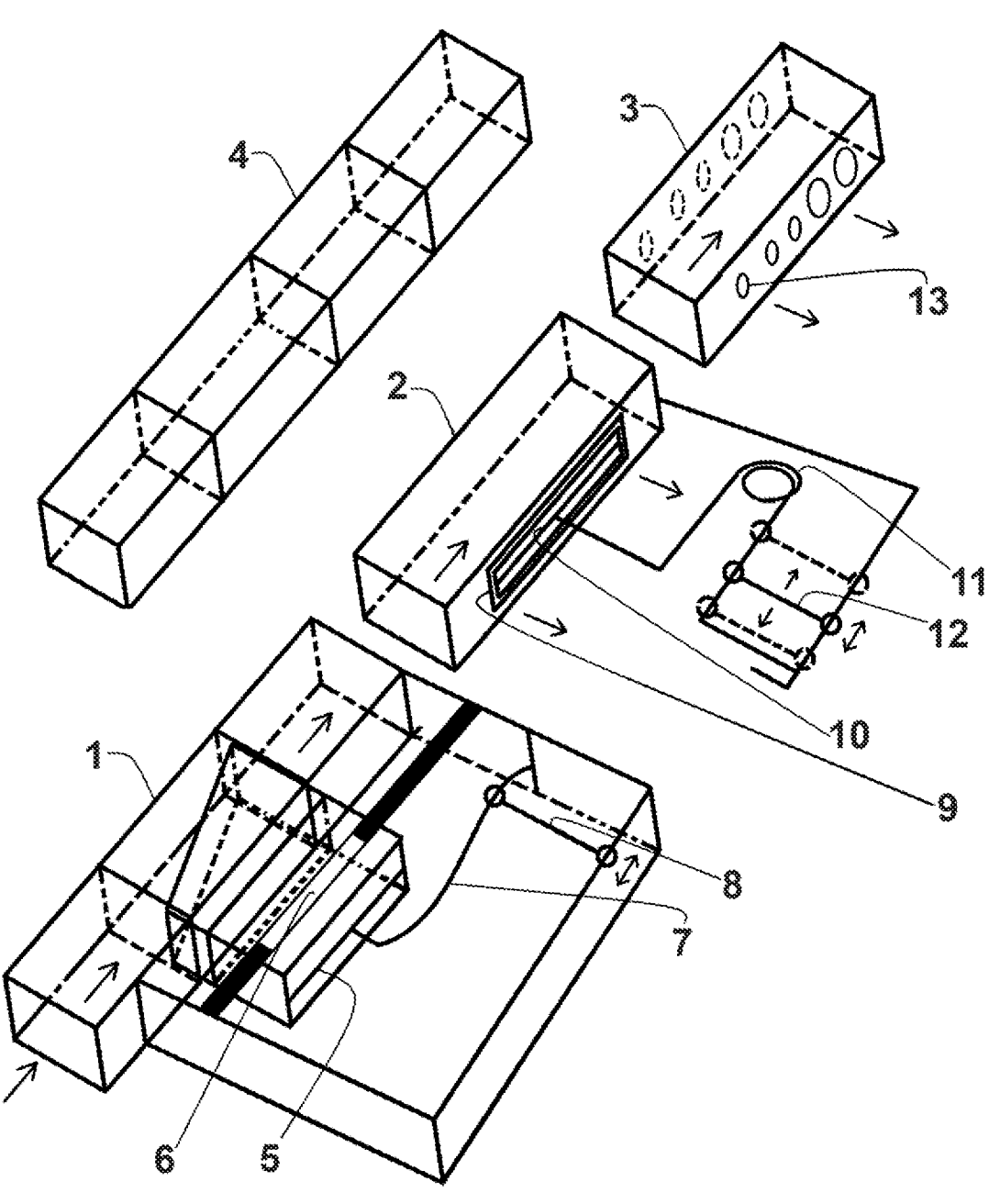
FIG. 2: General view of Rakan glaucoma device showing three parts separated with the sliding-seal piece moved apart for illustration.
Figure 3:
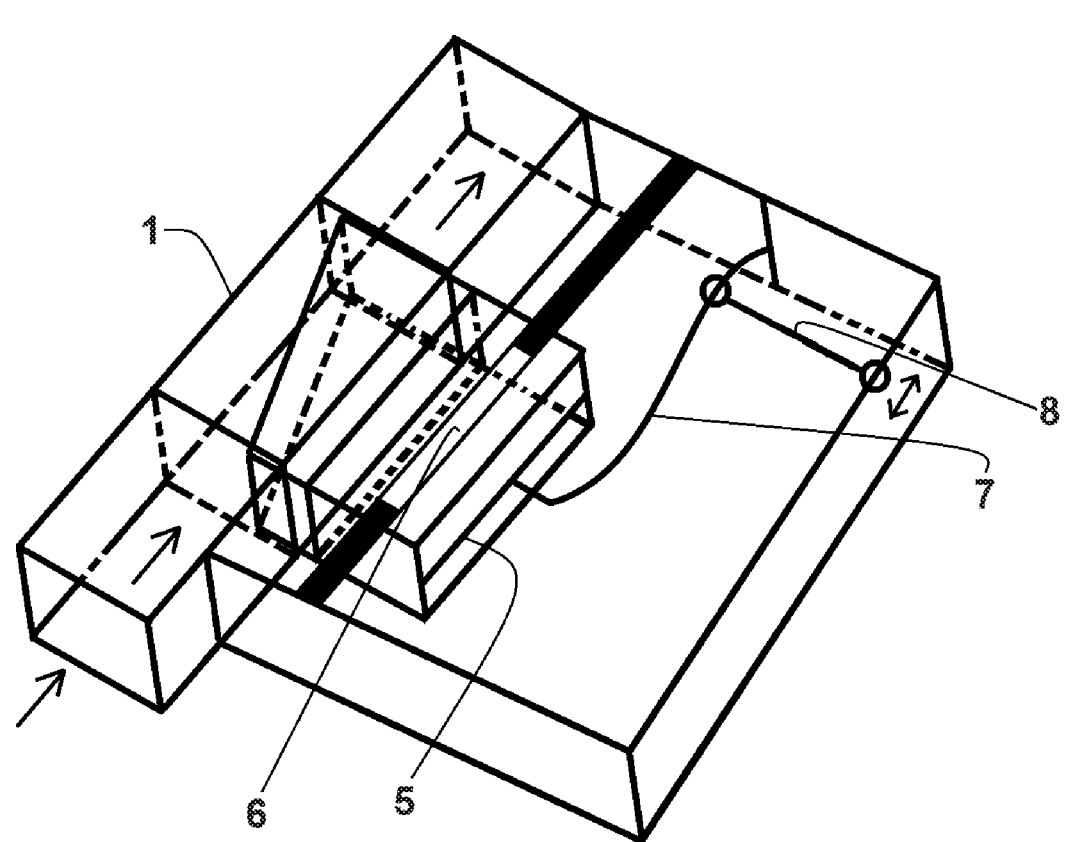
FIG. 3: First part of Rakan glaucoma device.
Figure 4:
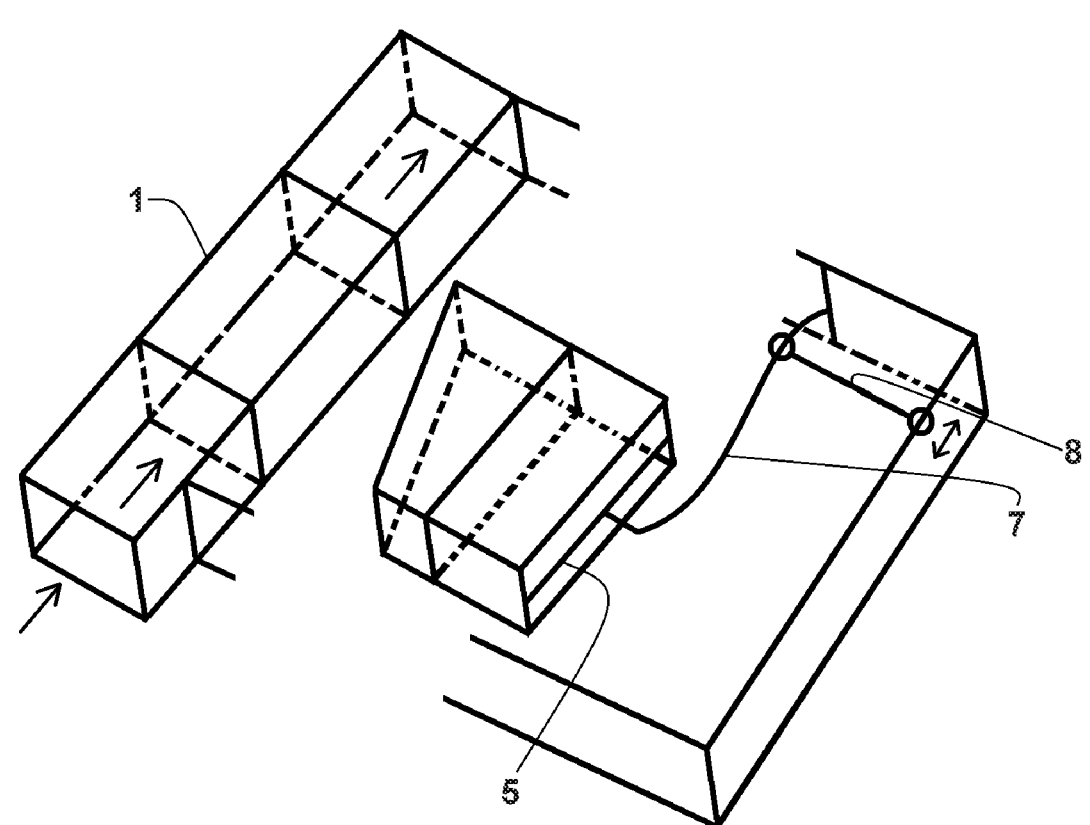
FIG. 4: Separated components of the first part showing indicator-valve-seal piece apart from tube for illustration.
Figure 6:
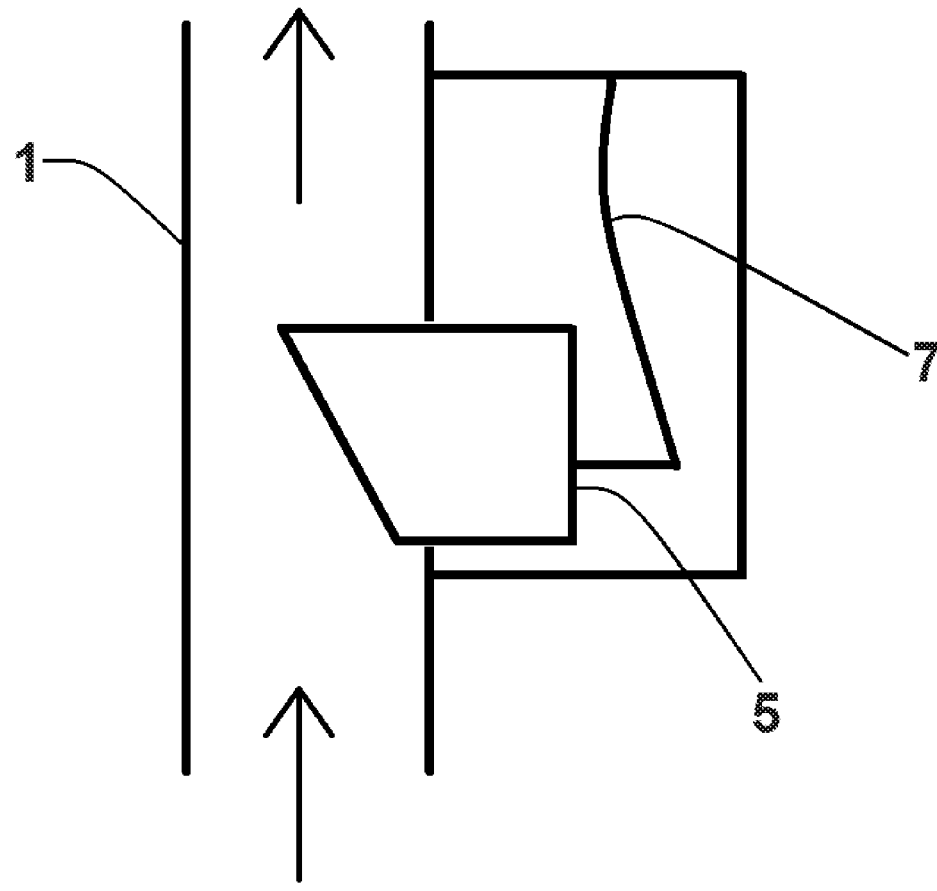
FIG. 6: Two-dimensional view of the first part showing the indicator-valve-seal piece in open position.
Figure 7:
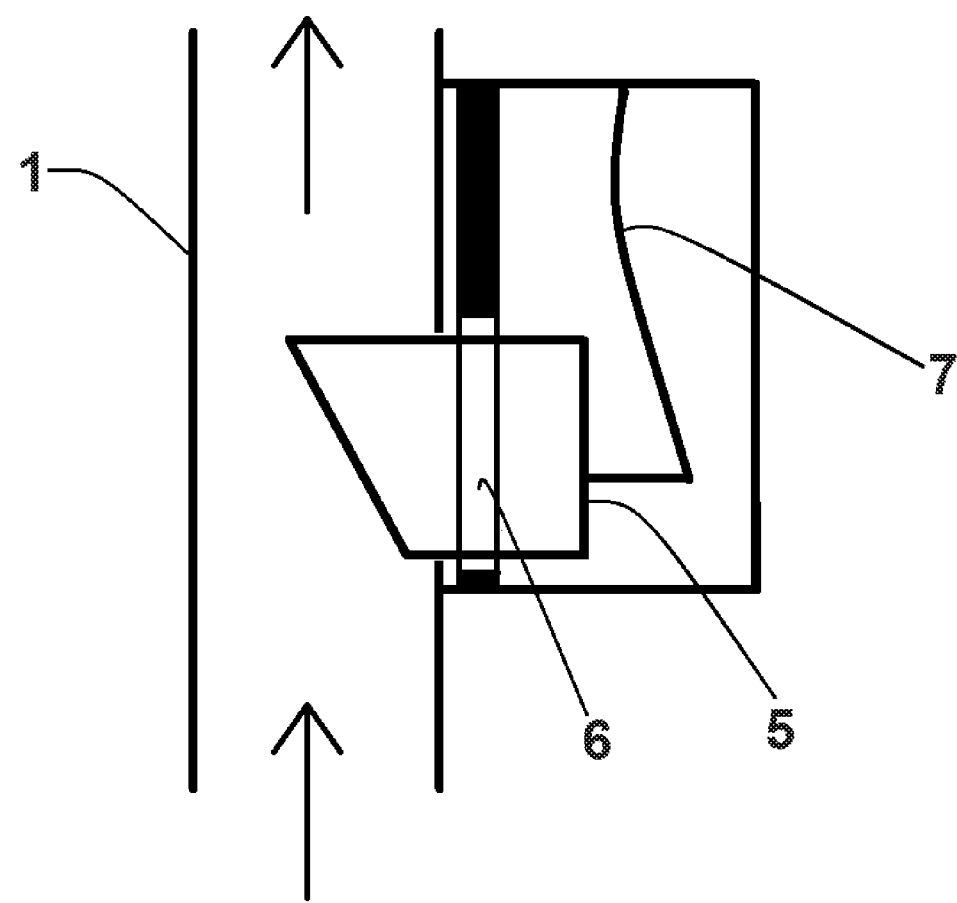
FIG. 7: Two-dimensional view of the first part showing the indicator-valve-seal piece in open position with indicator window.
Figure 11:
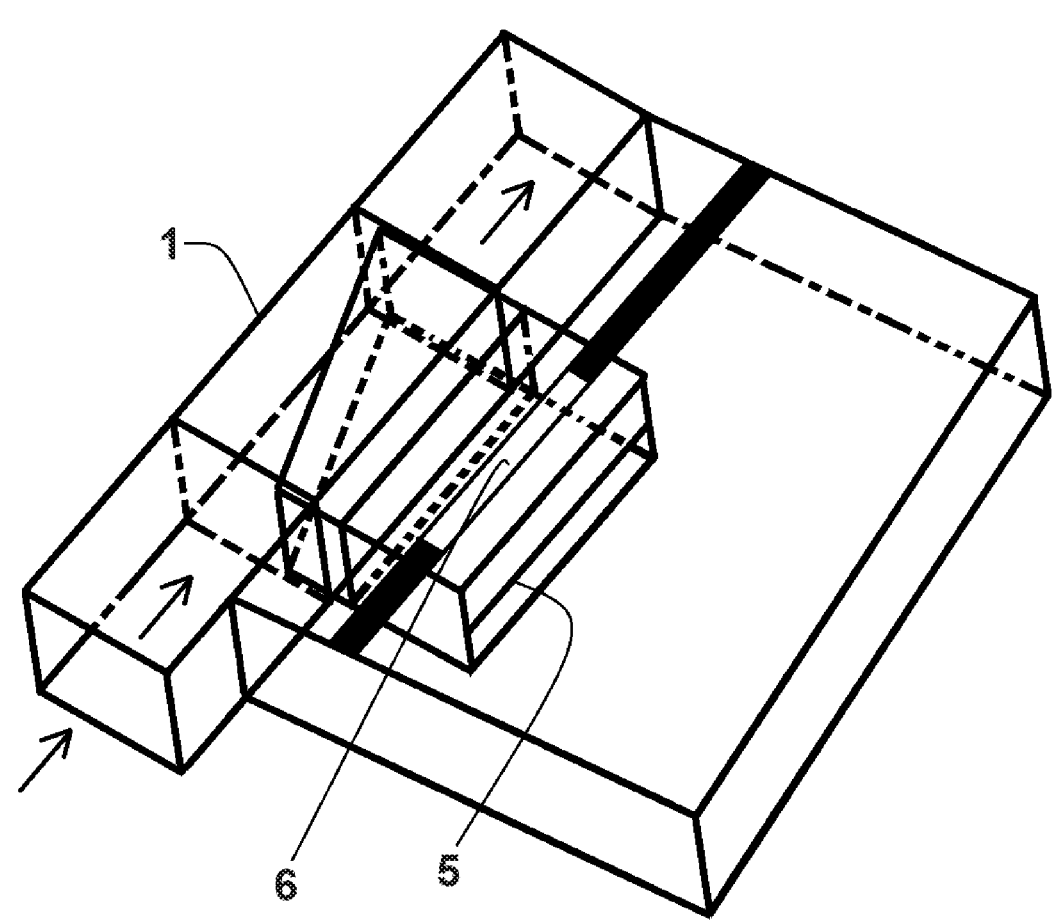
FIG. 11: First part of Rakan glaucoma device using a contained-pressure container instead of spring.
Figure 12:
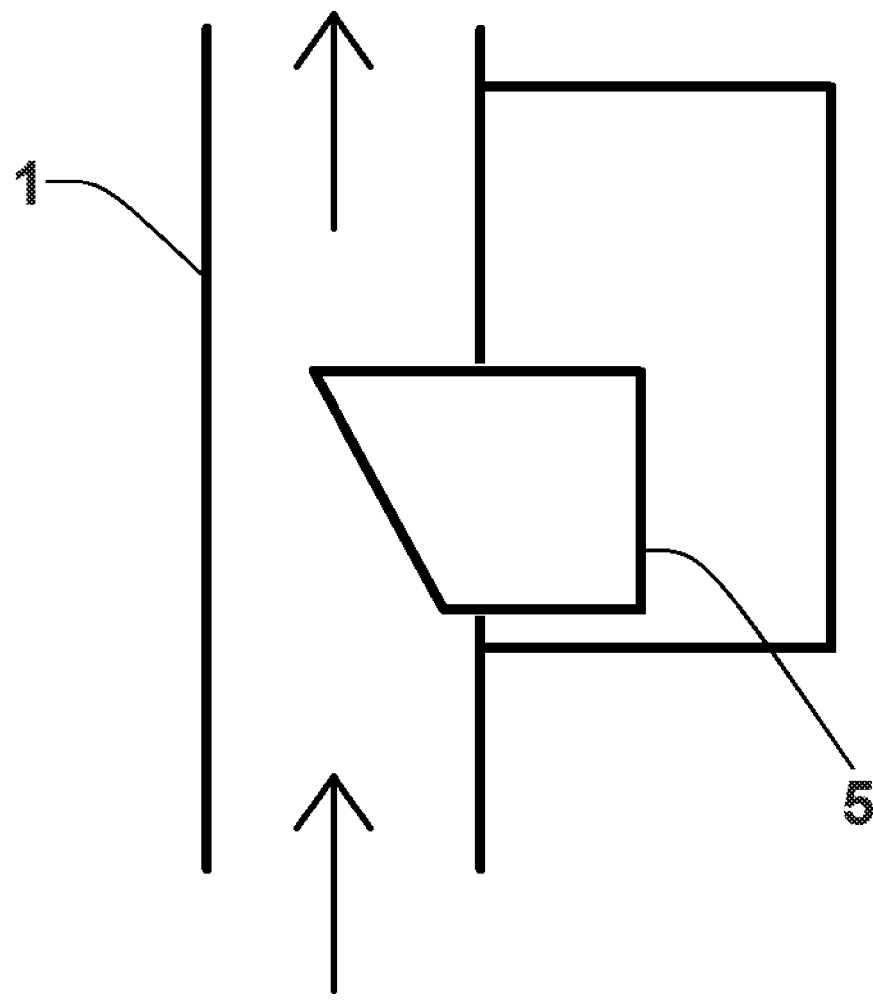
FIG. 12: Two-dimensional view of the first part using a contained-pressure container instead of spring.
Figure 26:
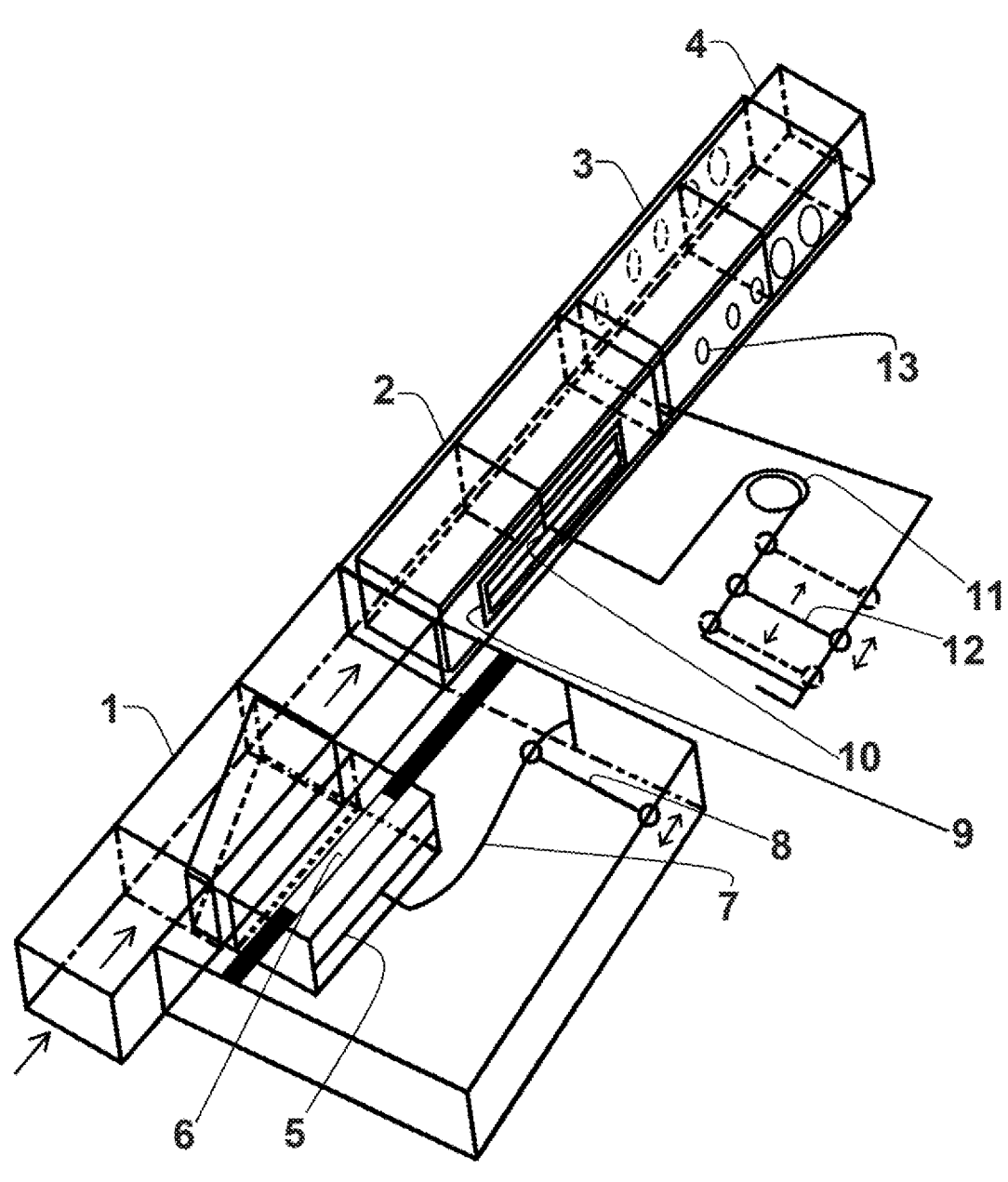
FIG. 26: General view of Rakan glaucoma device with sliding-seal piece blunt-sealing second and third parts completely.
Figure 27:
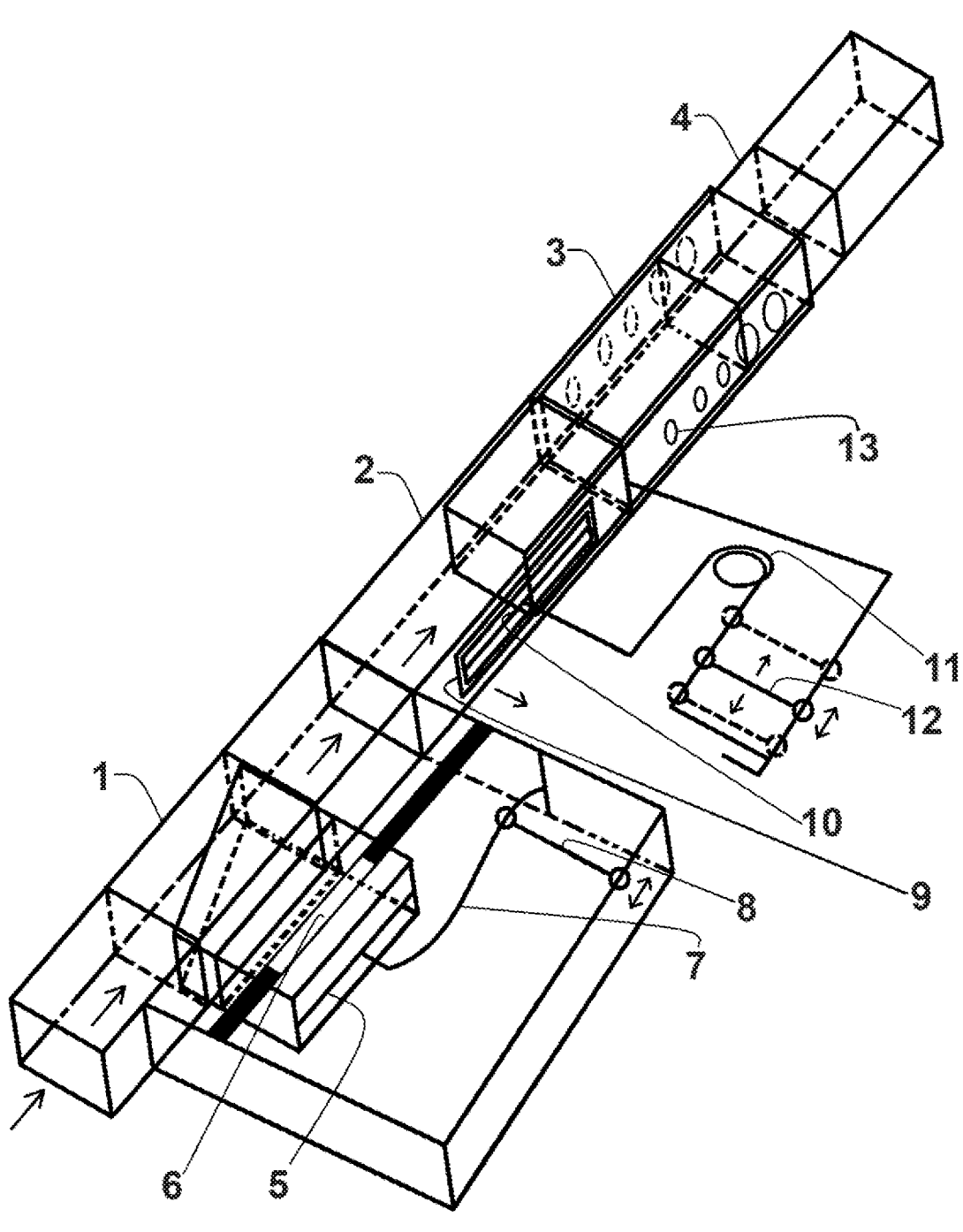
FIG. 27: General view of Rakan glaucoma device with sliding-seal piece blunt-sealing portion of second part and all of third part.
Figure 28:
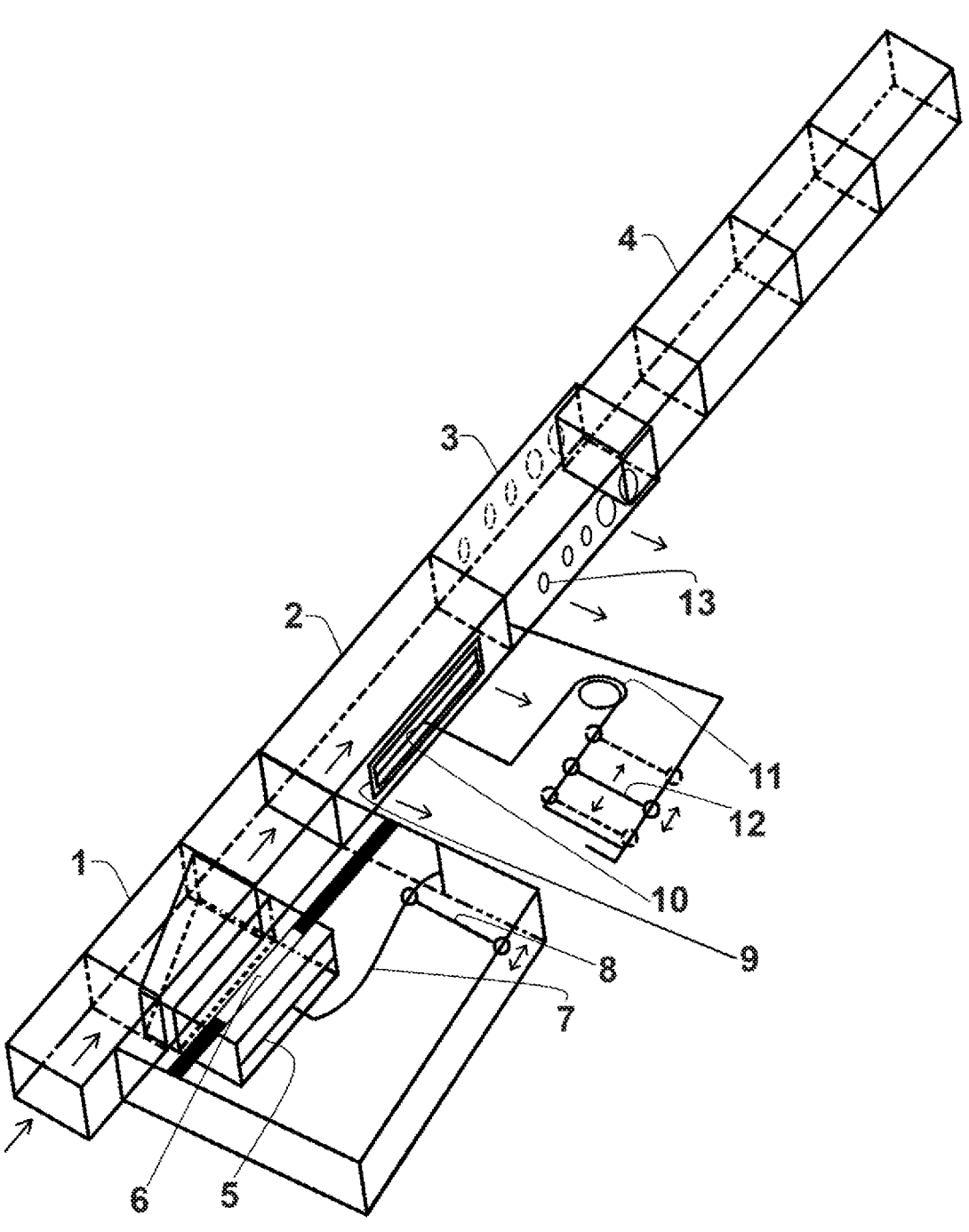
FIG. 28: General view of Rakan glaucoma device with sliding-seal piece blunt-sealing small portion of third part.

Rakan glaucoma device FIG. 1/FIG. 2/FIG. 26/FIG. 27/FIG. 28 consists of three parts. The first part FIG. 3/FIG. 4/FIG. 5/FIG. 6/FIG. 7/FIG. 8/FIG. 9/FIG. 10/FIG. 11/FIG. 12 comprises a tube 1 which could be in different shapes, that has a surface-opening which is configured to fit an indicator-valve-seal piece 5. At one side, the indicator-valve-seal piece 5 has a direct contact with fluid/aqueous humor inside the tube 1, with this fluid having a pressure hence generating force on the contacted side. At opposite/ another side, there is a counteracting/opposing pressure/ force generated by a contained-pressure container FIG. 11/FIG. 12 or by a spring structure 7 which could be in different shapes and that may have an adjustable piece 8 for adjusting power of the spring, as by moving the adjustable piece 8 in the directions shown by the illustrating-surrounding arrows, the length of arm will be adjusted hence adjusting the needed power to squeeze or release the spring 7.

Figure 5:
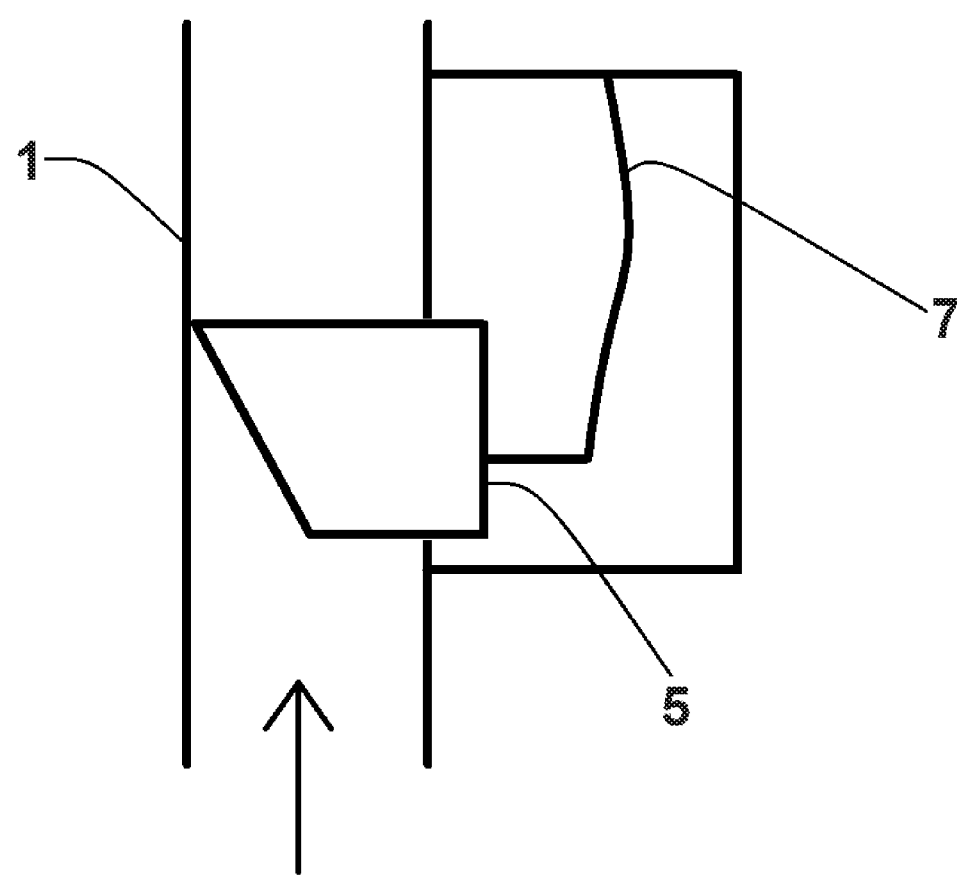
FIG. 5: Two-dimensional view of the first part showing the indicator-valve-seal piece in closed position.
Figure 8:
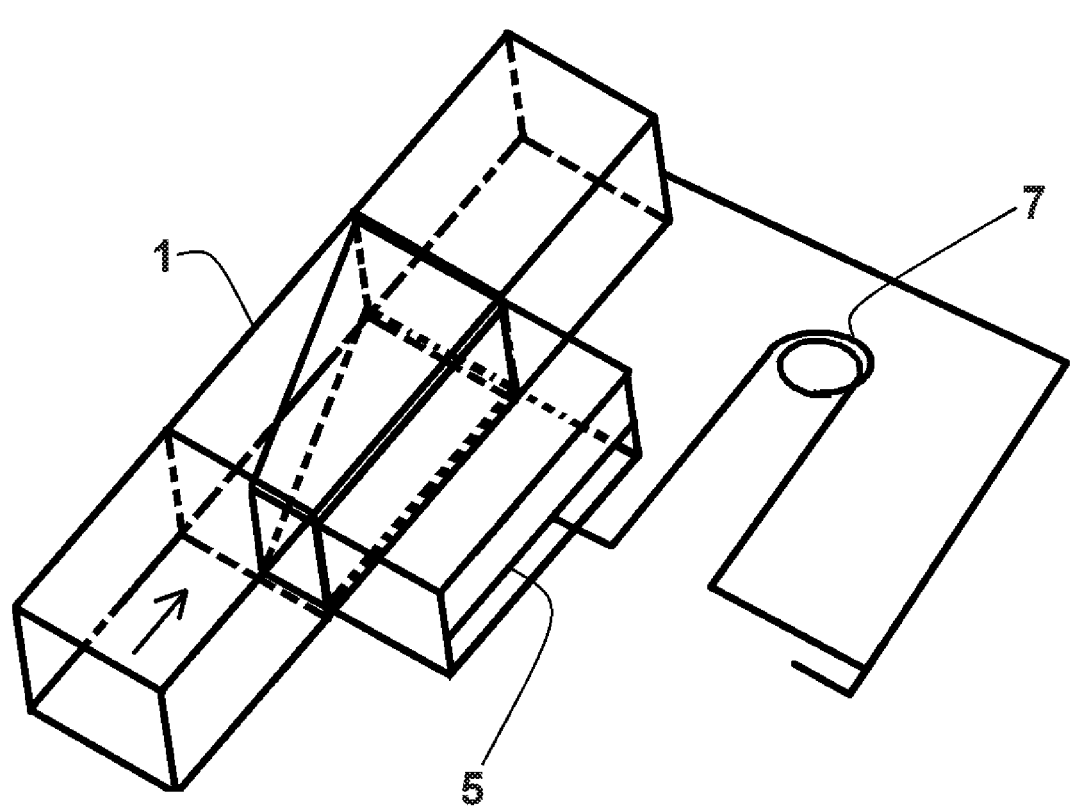
FIG. 8: First part of Rakan glaucoma device using a different-shape spring while the indicator-valve-seal piece in closed position.
Figure 9:
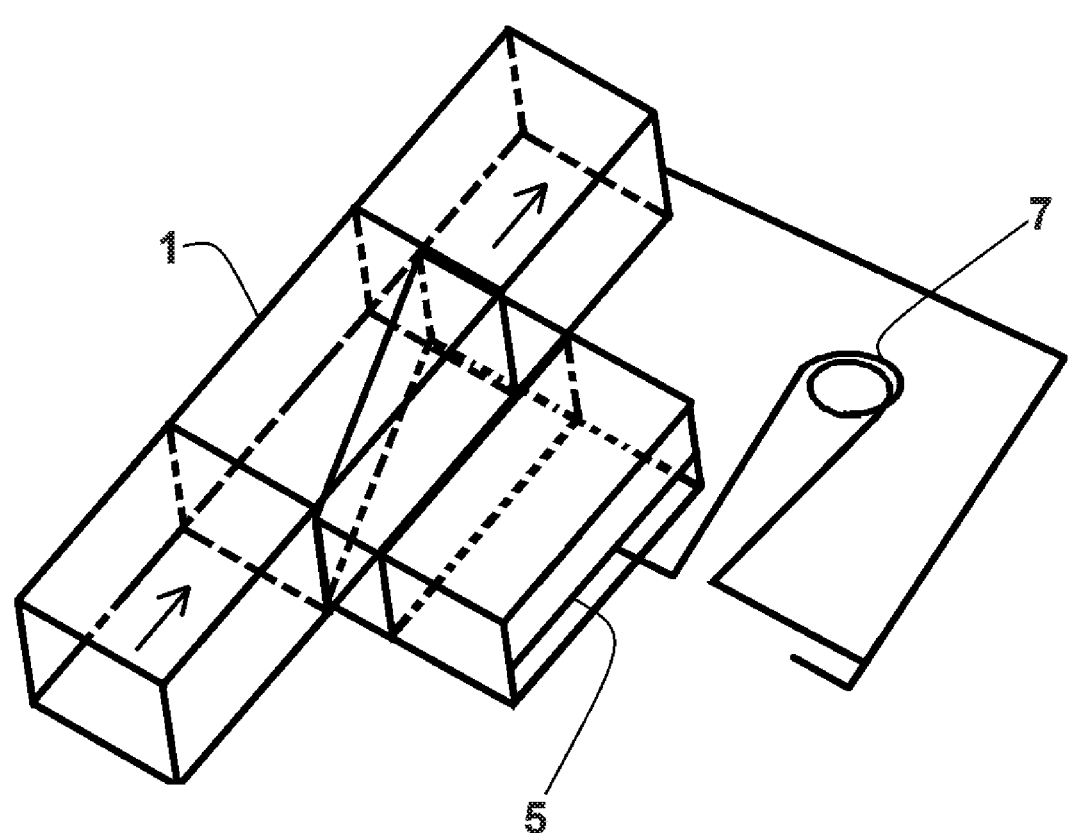
FIG. 9: First part of Rakan glaucoma device using a different-shape spring while the indicator-valve-seal piece in open position.
Figure 10:
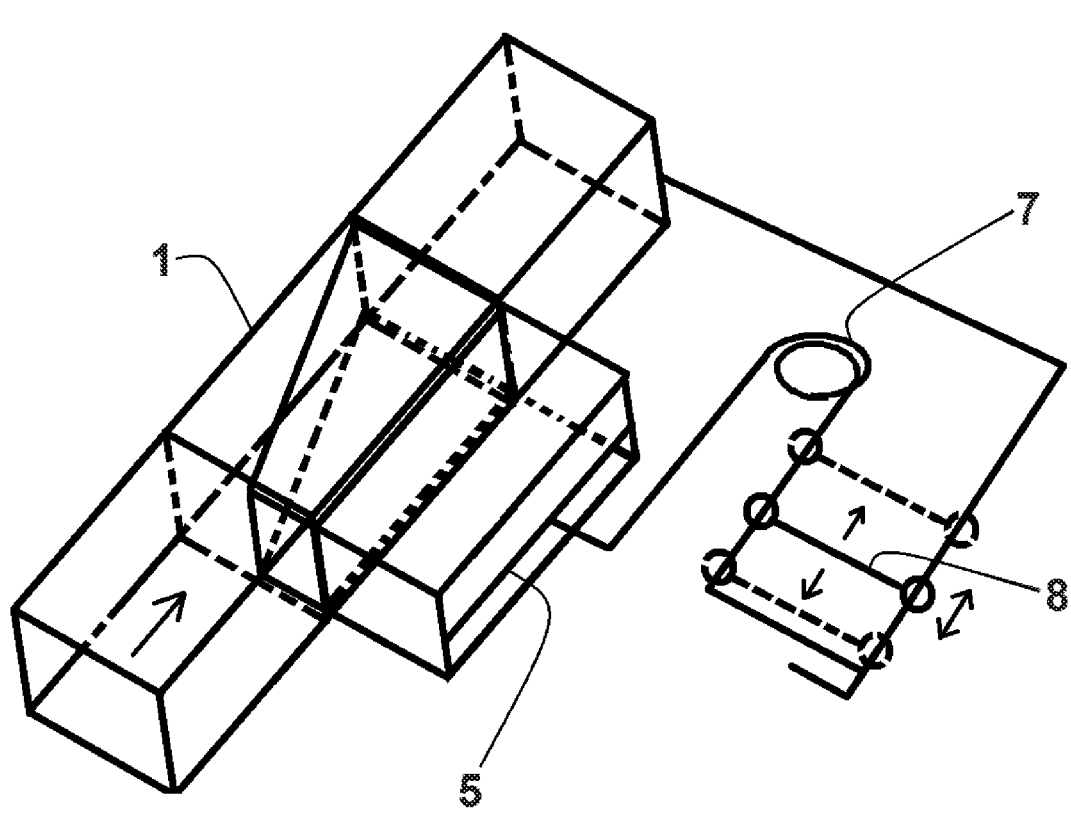
FIG. 10: First part of Rakan glaucoma device using a different-shape spring with a spring-adjusting piece while the indicator-valve-seal piece in closed position.

The difference between the two pressures/forces-on the opposing sides-determines the direction and the amount of movement of the indicator-valve-seal piece 5, as if the fluid pressure/force is less than the counteracting pressure/force, then the indicator-valve-seal piece 5 will be in closed position by getting displaced towards the inside of the tube hence closing/sealing the tube and preventing flow of the fluid/aqueous humor as shown in FIG. 5/FIG. 8/FIG. 10 with the arrow inside the tube showing the direction of fluid flow. And if the fluid pressure/force is more than the counteracting pressure/force, then the indicator-valve-seal 5 piece will be in open position by getting displaced away from the inside of the tube hence opening the tube and allowing flow of the fluid as shown in FIG. 1/FIG. 2/FIG. 3/FIG. 6/FIG. 7/FIG. 9/FIG. 11/FIG. 12/FIG. 26/FIG. 27/FIG. 28 with arrows inside the tube showing the direction of the fluid flow.

The indicator-valve-seal piece 5 has a color and/or number scale that can be seen through an indicator window 6, and as the difference between the two pressures/forces is variable and depends mainly on the change of fluid pressure, the amount of displacement of the indicator-valve-seal piece 5 is variable and depends mainly on the change of fluid pressure, hence different color and/or number would be seen through the indicator window 6 that reflects fluid/aqueous humor pressure.

Figure 13:
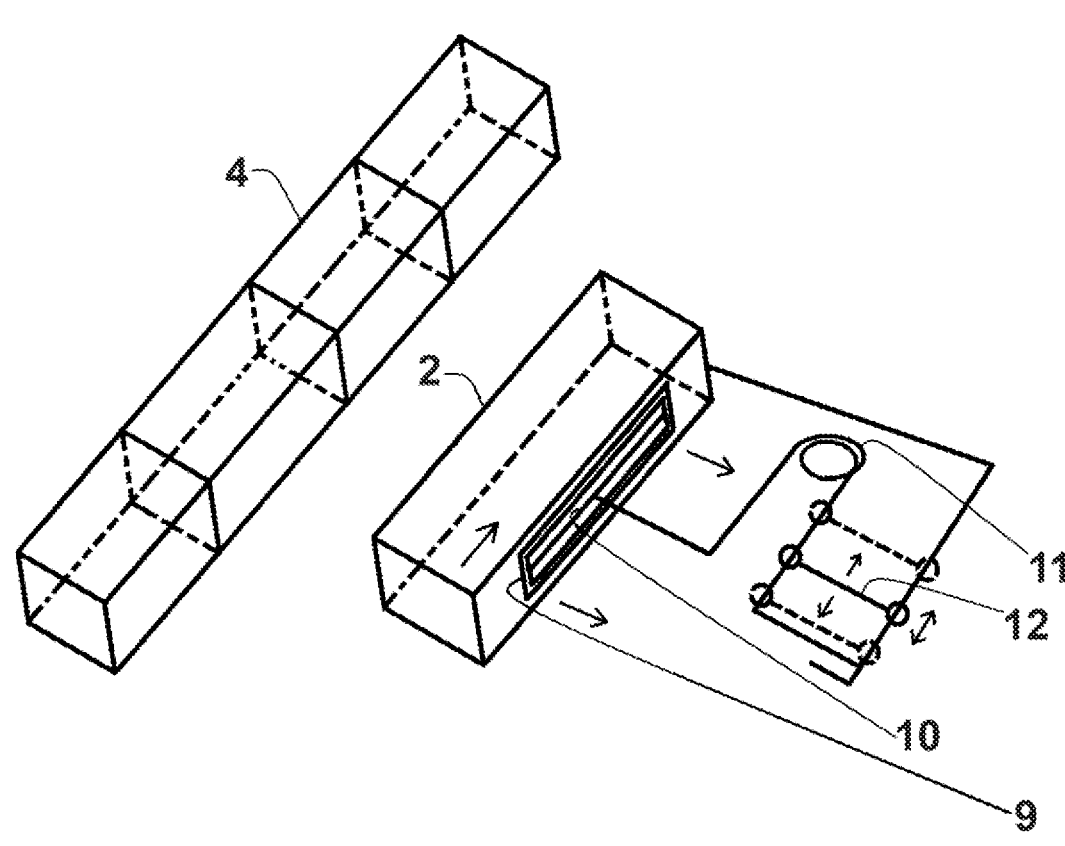
FIG. 13: Second part of Rakan glaucoma device with sliding-seal piece moved apart for illustration.
Figure 14:
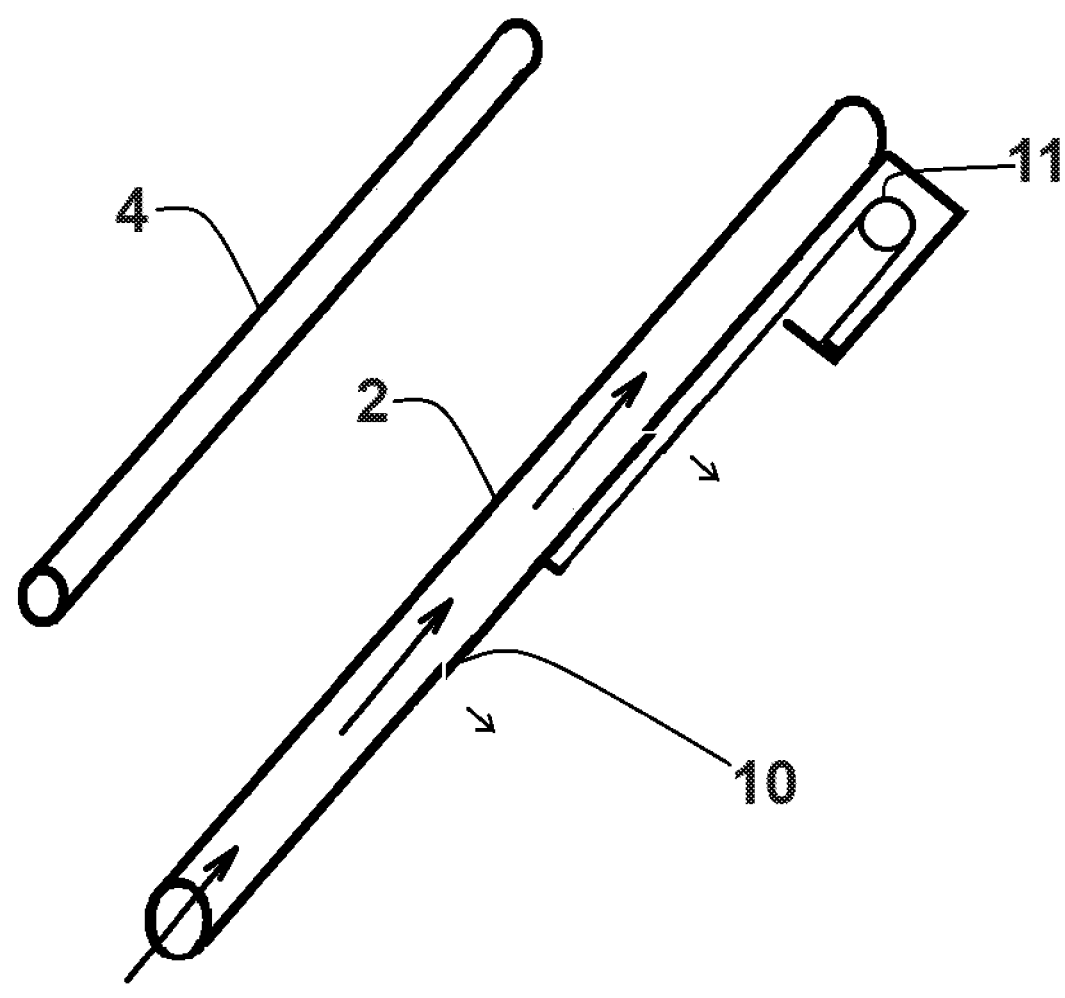
FIG. 14: Second part of Rakan glaucoma device using a cylindrical-shaped tube with sliding-seal piece moved apart for illustration.
Figure 15:
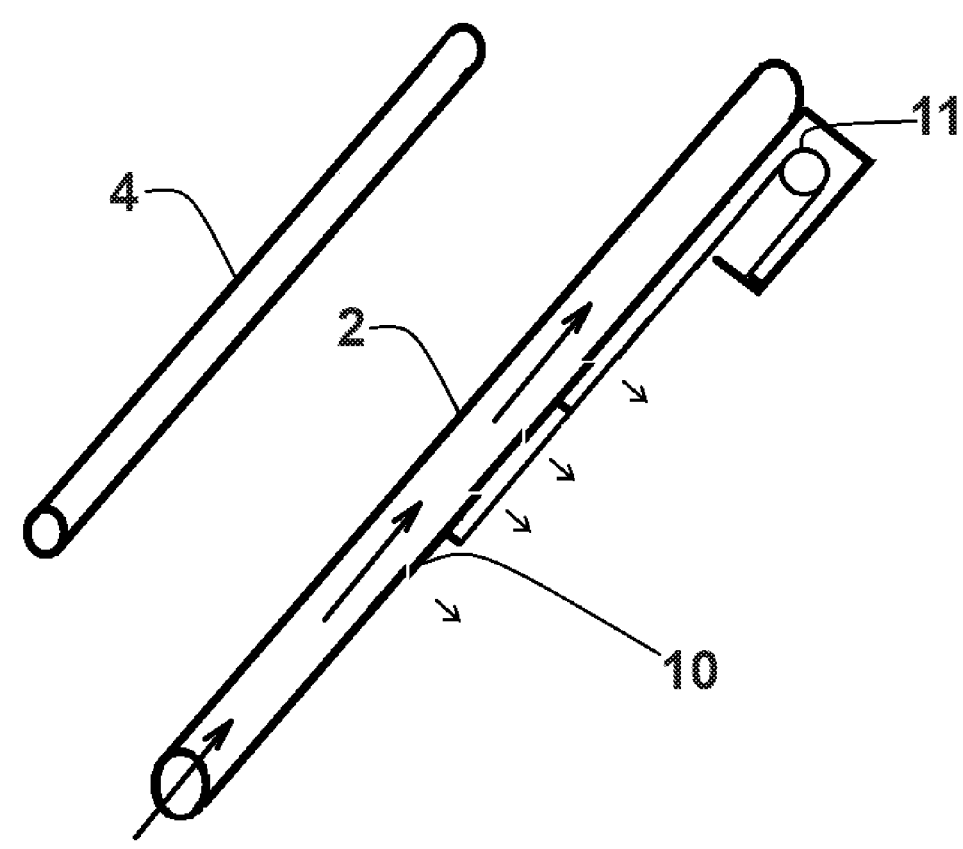
FIG. 15: Second part of Rakan glaucoma device using a cylindrical-shaped tube with two tube-surface-valve openings and sliding-seal piece moved apart for illustration.
Figure 16:
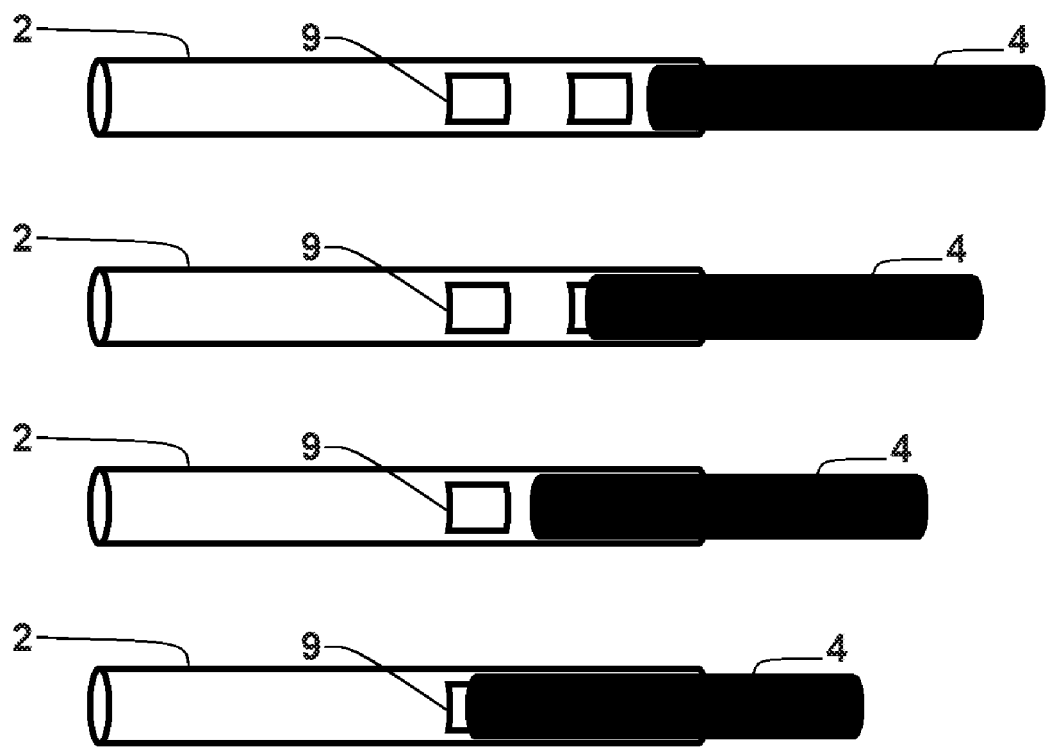
FIG. 16: Side view of second parts with two tube-surface-valve openings showing sliding-seal piece blunt-sealing the openings at different levels.
Figure 17:
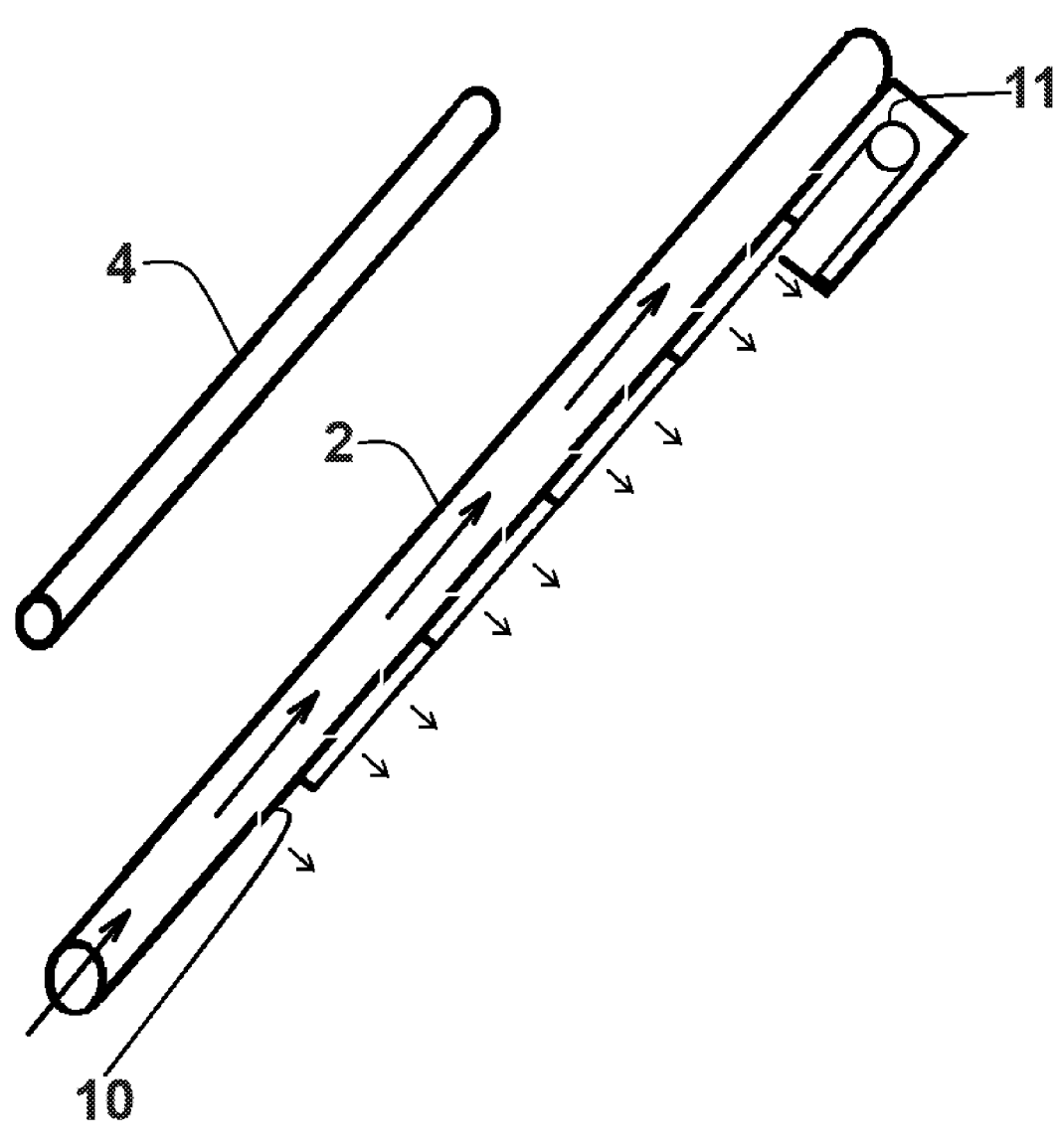
FIG. 17: Second part of Rakan glaucoma device using a cylindrical-shaped tube with five tube-surface-valve openings and sliding-seal piece moved apart for illustration.
Figure 18:
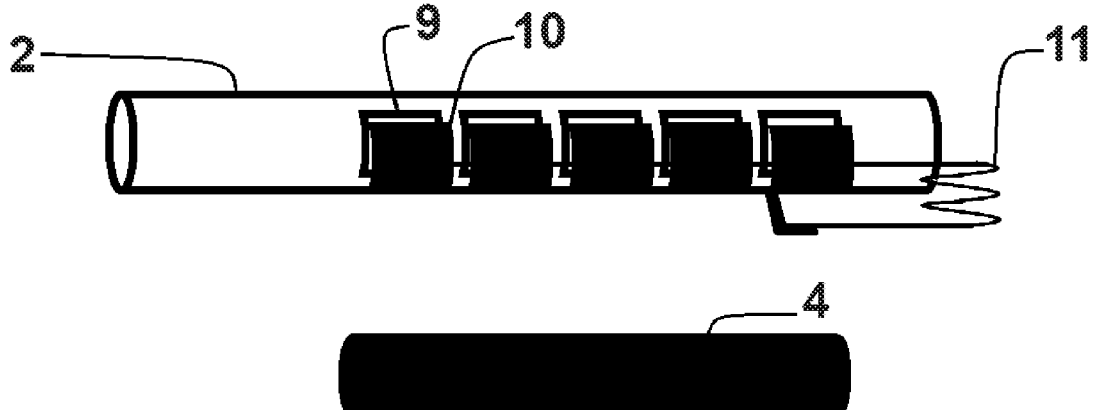
FIG. 18: Side view of second part showing valves in an open position as valve-cover pieces are displaced away from tube-surface-valve openings and sliding-seal piece moved apart for illustration.
Figure 19:
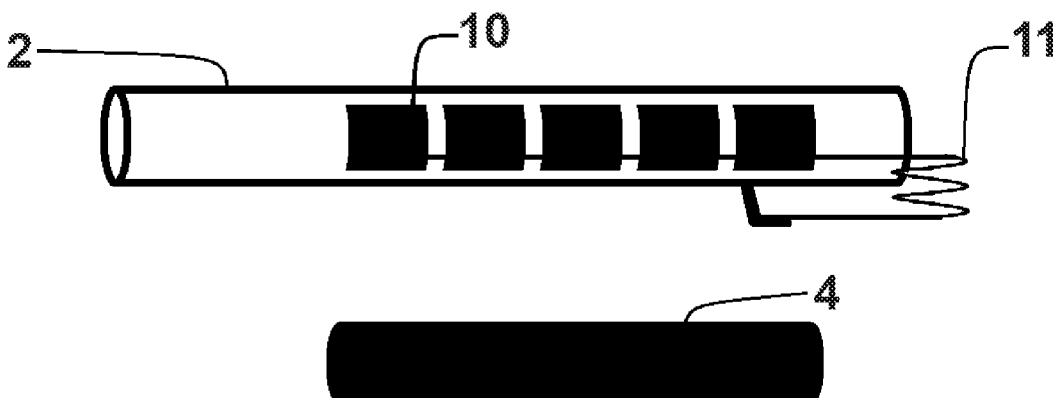
FIG. 19: Side view of second part showing valves in a closed position as tube-surface-valve openings are sealed with valve-cover pieces and sliding-seal piece moved apart for illustration.
Figure 20:
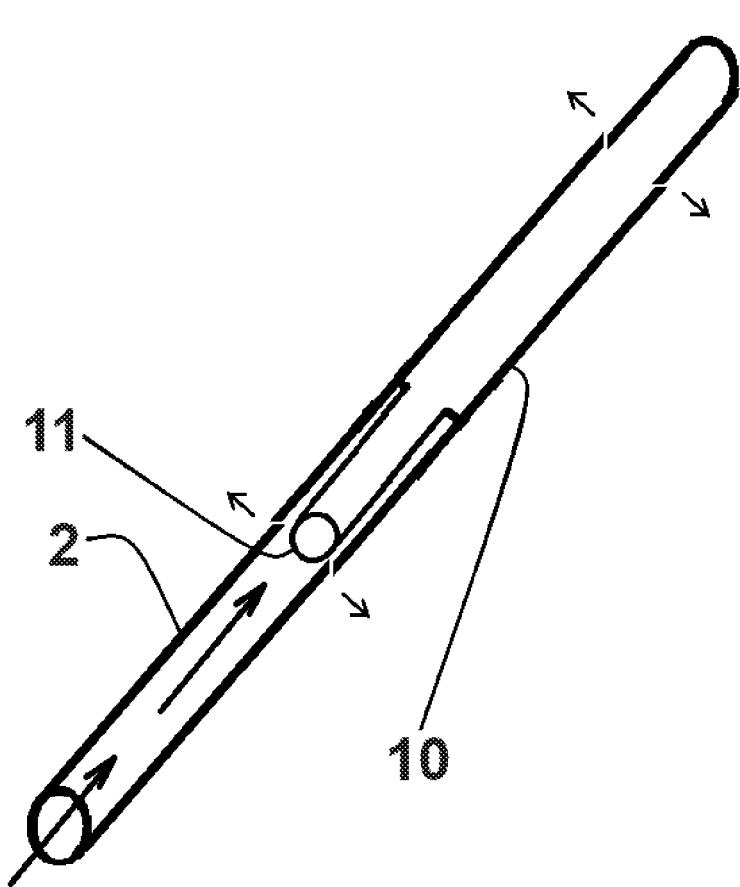
FIG. 20: Different design of second part with spring connected to two valve-cover pieces from inside the tube.
Figure 21:
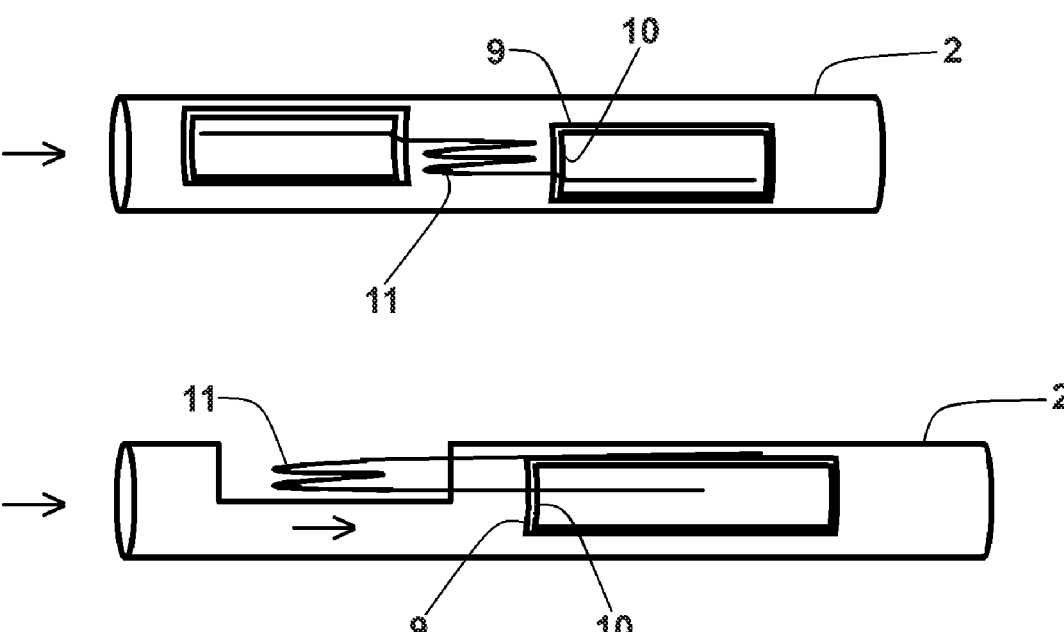
FIG. 21: Side view of different designs of the second part.
Figure 22:
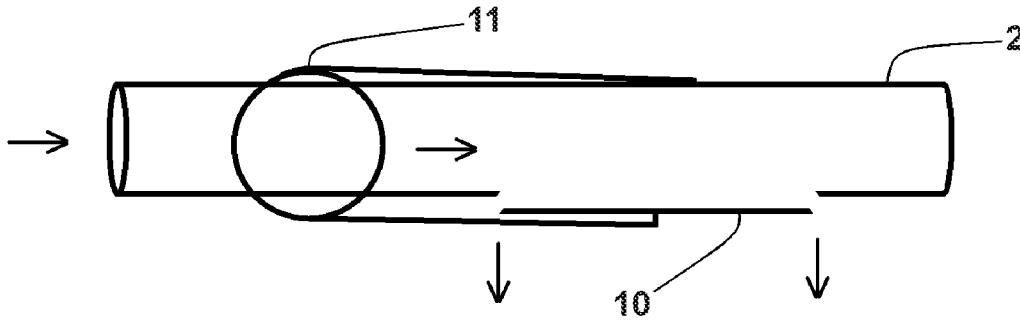
FIG. 22: Above view of different designs of the second part.
Figure 22:
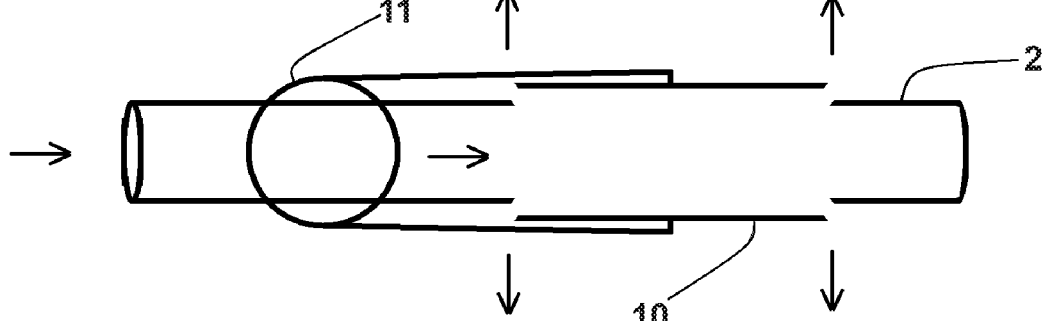
Figure 23:
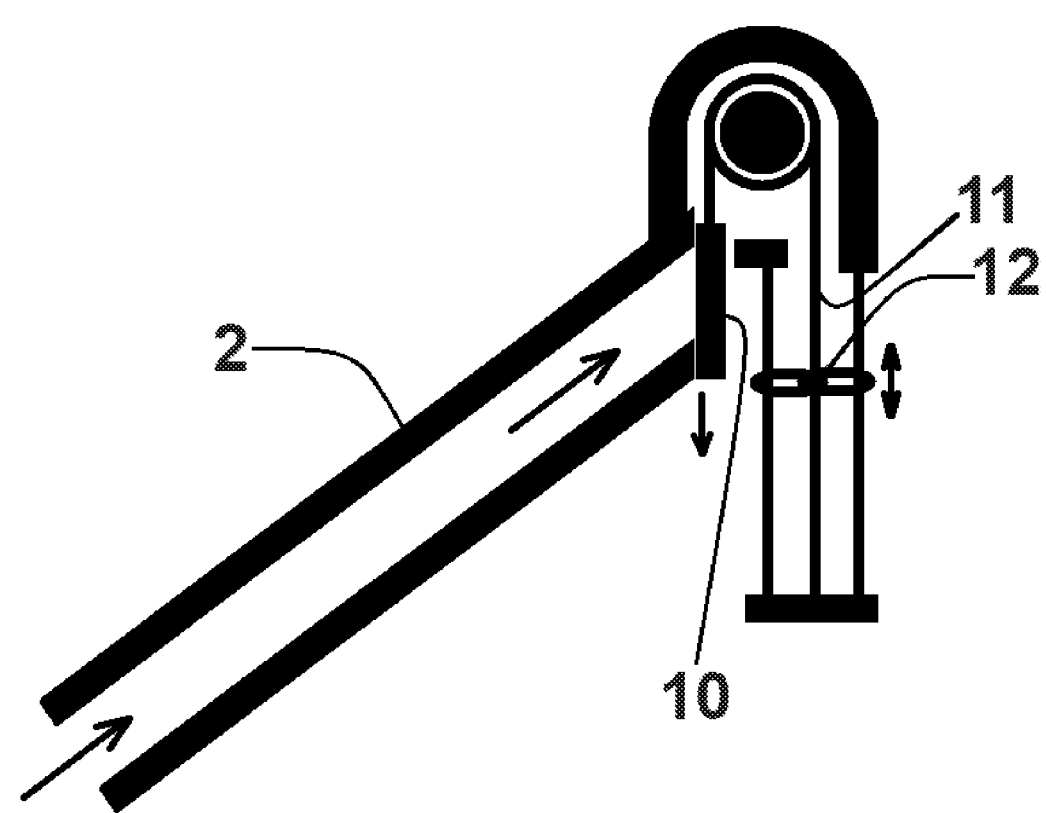
FIG. 23: Different design of second part which does not involve a sliding-seal piece and has no connection to third part of Rakan glaucoma device.

The second part FIG. 13/FIG. 14/FIG. 15/FIG. 16/FIG. 17/FIG. 18/FIG. 19/FIG. 20/FIG. 21/FIG. 22/FIG. 23 comprises a tube 2 which could be in different shapes and that has a tube-surface-valve opening 9 which is configured to be sealed by valve-cover piece 10. The second part 2 also comprises a sliding-seal piece 4, that is a blunt structure and it is configured to slide inside and blunt-seal the tube 2 lumen. The valve-cover piece is connected to a spring 11 that applies force on one side of the valve-cover piece 10 and pushes it against the tube-surface-valve opening 9 in order to seal it, while on the opposing side of the valve-cover piece 9 there is an opposing force that is generated by the pressure of the fluid/aqueous humor inside the tube 2. The difference between the two forces on the opposing sides determines the position of the valve-cover piece, as if the fluid pressure/ force is less than the opposing force generated by spring 11, then the second part valve will be in closed position FIG. 19, as the tube-surface-valve opening 9 is sealed by valve-cover piece 10. And if the fluid pressure/force is more than the opposing force generated by spring 11, then the second part valve will be in open position FIG. 18, as the valve-cover piece 10 is displaced away from the tube-surface-valve opening 9 which allows fluid/aqueous humor drainage out of the tube hence decreasing intraocular pressure. The tube 2 could have one tube-surface-valve opening 9 and one valve-cover piece 10 as shown in FIG. 14 or more as shown in FIG. 15/FIG. 17 and the spring and openings could be in different designs and orientations FIG. 20/FIG. 21/FIG/22.

The force generated by the fluid/aqueous humor pressure depends on the size of surface area that is exposed to and in contact with the fluid, hence using the sliding-seal piece 4 to adjust the area of the valve-cover piece/pieces 10 that is exposed to fluid pressure FIG. 26/FIG. 27/FIG. 28 would adjust the generated force that opposes the force generated by the spring 11 as shown in FIG. 16 and by this we can adjust the amount of fluid/aqueous humor pressure needed to open valve and drain fluid out of the eye, hence adjusting intraocular pressure. Furthermore, the second part spring 11 could be in different shapes and it may have an adjustable piece 12 for adjusting power of the spring, as by moving the adjustable piece 12 in the directions shown by the illustrating-surrounding arrows, the length of arm will be adjusted hence adjusting the needed power to squeeze or release the spring 11. So, using the sliding-seal piece 4 and the adjustable piece 12 would allow us to precisely control the amount of fluid outflow/drainage and intraocular pressure. The sliding-seal piece 4 is used with both second and third part of Rakan glaucoma device, however, the second part could be in a different design FIG. 23 without using sliding-seal piece 4 and without being connected to the third part.

Figure 24:
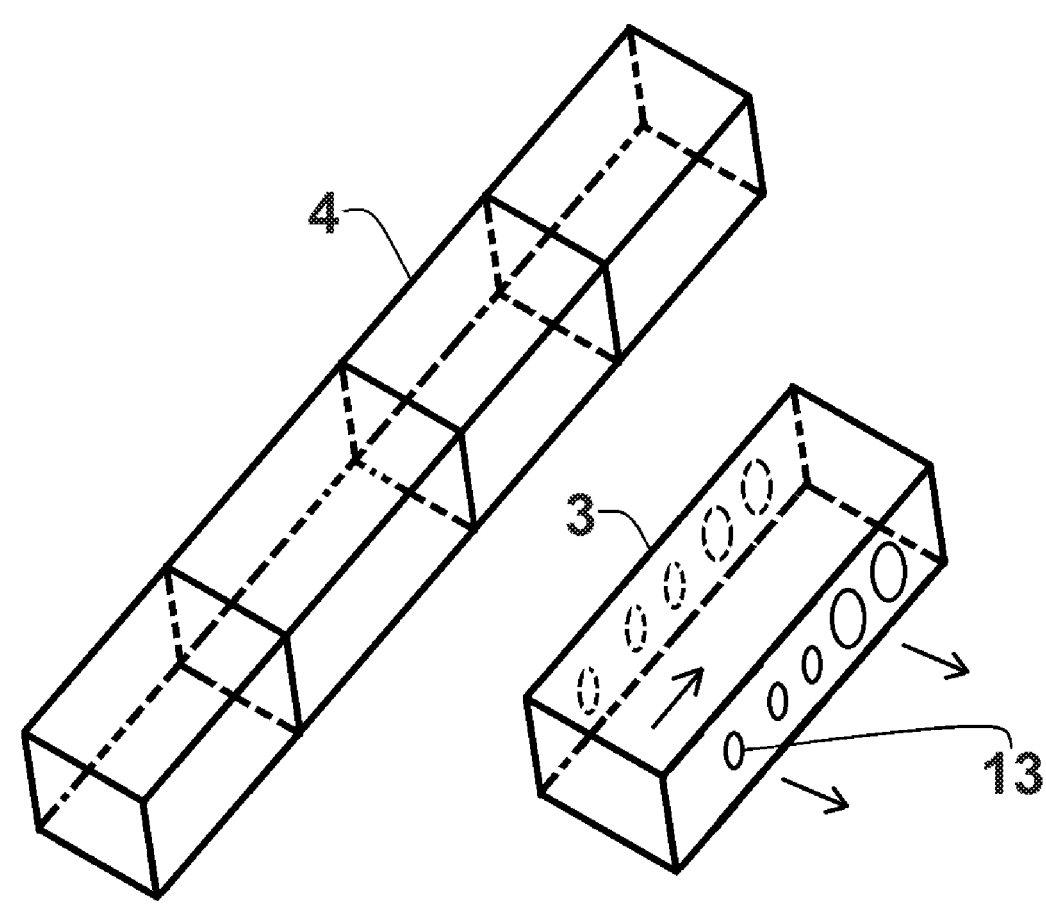
FIG. 24: Third part of Rakan glaucoma device with sliding-seal piece moved apart for illustration.
Figure 25:
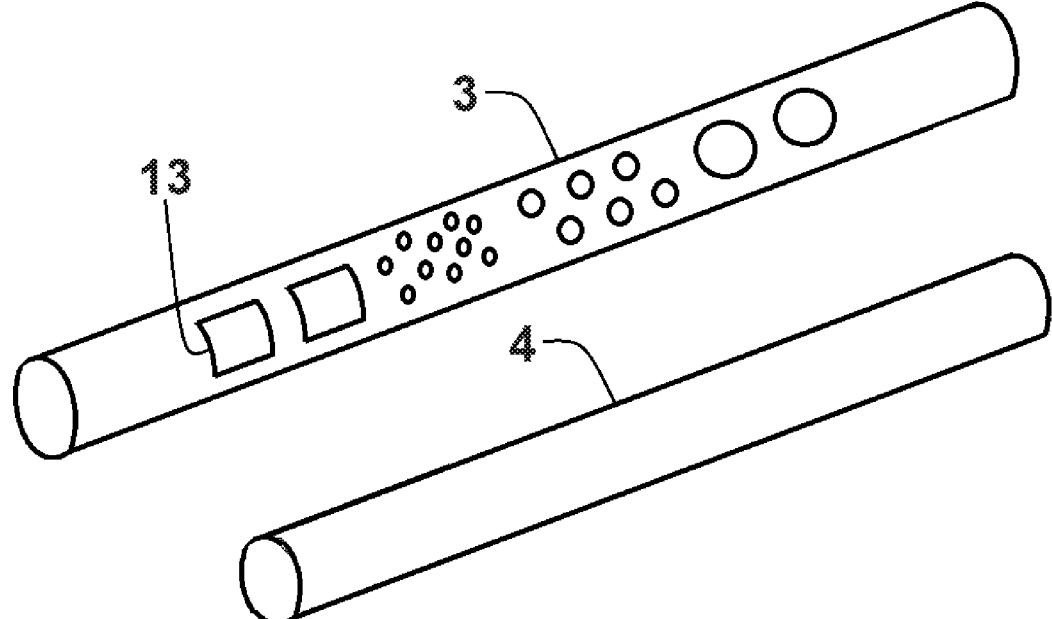
FIG. 25: Third part using a cylindrical-shaped tube with different shapes and sizes of tube-surface openings with sliding-seal piece moved apart for illustration.

The third part FIG. 24/FIG. 25 comprises a tube 3 which could be in different shapes and that could have one surface-opening 13 or more that could be in different shapes which is configured to be sealed from inside the tube 3 by the sliding-seal piece 4. The sliding-seal piece could be adjusted to blunt seal all the surface-openings FIG. 26/FIG. 27 or to blunt-seal different numbers of the surface-openings FIG. 1/FIG. 28, and adjusting the number of the openings 13 sealed/unsealed determines the amount of aqueous humor/ fluid drainage hence adjusting intraocular pressure.

The invention claimed is:

1. An intraocular fluid drainage device for controlling an intraocular fluid pressure depending on an intraocular pressure in an eye of a patient, comprising:

a first part comprising a first tube having a first tube lumen, a second part comprising a second tube having a second tube lumen, and a third part comprising a third tube having a third tube lumen;

wherein said first part further comprises an indicator-valve-seal, an indicator window, and a first spring; said first tube is connected in the eye of the patient at a first distal end and to said second part at a first proximal end; said first tube having a first surface opening; said first surface opening is configured to receive the indicator-valve-seal; said indicator-valve-seal is a first moveable blunt structure comprising an indicator scale, wherein said indicator scale comprises colors and numbers; said indicator scale is configured to be seen through said indicator window; said indicator-valve-seal having a direct first fluid contacting side with an intraocular fluid inside said first tube having a first fluid pressure force reflecting the intraocular pressure; said first spring generating a first spring force at said opposing side of the indicator-valve-seal; said first spring having a first adjustable piece configured to adjust said first spring force needed to squeeze or release said first spring;

wherein a displacement of said indicator-valve-seal is determined by the difference between said first fluid pressure force and said first spring force;

wherein if said first fluid pressure force is less than said first spring force, said indicator-valve-seal would be displaced towards said first tube lumen therefore sealing said first tube and preventing fluid flow and drainage;

wherein if said first fluid pressure force is more than the first spring force; the indicator-valve-seal would be displaced away from said first tube lumen therefore opening the first tube, allowing flow and drainage of said intraocular fluid, and decreasing said intraocular pressure; wherein the size of said first tube lumen is proportional to said first fluid pressure force, therefore increasing fluid pressure increases the size of the opening and increases fluid flow and drainage;

wherein said colors and numbers shown through said indicator window indicates said displacement of the indicator-valve-seal, therefore indicates intraocular fluid pressure;

wherein said second part further comprises a sliding-seal, a valve-cover, and a second spring; said second tube is connected to the first part at a second distal end and to said third part at a second proximal end; said second tube having a tube-surface-opening; said second tube is configured to receive the sliding-seal; said sliding-seal is a second movable blunt structure configured to blunt-seal said second tube and said third tube from inside the second tube lumen and the third tube lumen, respectively; said tube-surface-opening is configured to be sealed by said valve-cover; said valve-cover is movable and having a direct second fluid contacting side with the intraocular fluid inside said second tube having a second fluid pressure force reflecting said intraocular pressure; said second spring generating an a second spring force at said opposing side of the valve-cover; said second spring having a second adjustable piece configured to adjust said second spring force needed to squeeze or release said second spring; said second fluid pressure force dependent on a size of area of said valve-cover exposed to said intraocular fluid; said size of area of said valve-cover exposed to said intraocular fluid is determined by moving said sliding-seal;

wherein said position of said valve-cover is determined by the difference between the second fluid pressure force and the second spring force;

wherein if the second fluid pressure force is less than the second spring force, the valve-cover would be in a closed position, wherein the valve-cover is displaced towards said tube-surface-opening therefore sealing said second tube and preventing fluid drainage;

wherein if said second fluid pressure force is more than said second spring force, said valve-cover would be displaced away from said tube-surface-opening therefore opening said second tube and allowing drainage of intraocular fluid and decreasing said intraocular pressure;

wherein said third tube is connected to the second part at a third distal end; said third tube having surface openings; said sliding-seal is configured to blunt-seal said surface openings from inside the third tube lumen; wherein moving the sliding-seal controls the sealing of a number and portion of surface openings therefore controlling said intraocular pressure.

* * * * *